United States Patent [19]

Arai et al.

[11] Patent Number: 4,921,705

[45] Date of Patent: May 1, 1990

[54] LIPID POWDER HAVING CROSS-LINKED COATING THEREON AND PROCESS FOR PREPARING SAME

[75] Inventors: Motoharu Arai; Masatsugu Ito, both of Tokyo, Japan

[73] Assignee: Nippon Oil and Fats Co., Ltd., Tokyo, Japan

[21] Appl. No.: 216,887

[22] Filed: Jul. 8, 1988

[30] Foreign Application Priority Data

Jul. 14, 1987 [JP] Japan ................... 62-173825

[51] Int. Cl.$^5$ .............................................. A61K 9/48
[52] U.S. Cl. ........................... 424/450; 424/491; 424/498; 428/402; 428/403
[58] Field of Search ............. 424/491, 492, 493, 494, 424/498, 450; 514/2, 21; 428/402, 403

[56] References Cited

U.S. PATENT DOCUMENTS

| | | | |
|---|---|---|---|
| 3,549,555 | 12/1970 | Hiestand et al. | 424/492 |
| 3,886,084 | 5/1975 | Vassiliades | 424/494 |
| 3,956,172 | 5/1976 | Sacki et al. | 424/492 |
| 4,376,113 | 3/1983 | Suglia et al. | 424/492 |
| 4,402,856 | 9/1983 | Schnoring et al. | 424/492 |
| 4,492,714 | 1/1985 | Cooper et al. | 426/602 |
| 4,515,769 | 5/1985 | Merritt et al. | 424/49 |

*Primary Examiner*—Jacqueline M. Stone
*Assistant Examiner*—Jean Witz
*Attorney, Agent, or Firm*—Majestic, Parsons, Siebert & Hsue

[57] ABSTRACT

A lipid powder having a cross-linked coating thereon comprises a core lipid powder and a water-soluble coating agent coating the core lipid powder. The water-soluble coating agent contains cross-linked protein. A process for preparing lipid powders each having a cross-linked coating thereon comprises the steps of emulsifying lipid and a water-soluble coating agent containing protein to obtain an emulsion, adding a cross-linking agent for the protein the the emulsion to thereby cross-link the protein, atomizing and drying the emulsion containing the cross-linked protein to terminate the cross-linking reaction and to obtain lipid powders each coated with the water-soluble coating agent, and cooling the coated lipid powders.

11 Claims, No Drawings

LIPID POWDER HAVING CROSS-LINKED COATING THEREON AND PROCESS FOR PREPARING SAME

BACKGROUND OF THE INVENTION

This invention relates to a lipid powder having a cross-linked coating thereon and employed as a raw material or an additive in the sectors of foodstuffs or feeds, and to a process for producing the lipid powder.

Researches have long been made for evolving a suitable process for preparing lipid powders. Recently, oily substances exhibiting certain physiological activities, such as eicosapentaenoic acid (EPA) or tocopherol, are attracting public attention since they have proven properties favorable to health and prevention of senility. It has been desired that these substances be available in the form of lipid powder, because they are stable and easy to handle when in this form. For example, there is known a process of emulsifying an oily substance in an aqueous phase containing protein, hydrocarbon, cellulose, gum or the like dissolved therein and forming powders of the oily substance by atomizing and drying, as disclossed in Japanese Laid-open Patent Publications Nos. 1415/1966 and 11040/1975. The process, however, has disadvantages in that the powder obtained thereby has a low barrier capacity to oxygen, while the oily substances containing higher unsaturated fatty acids are oxidized in a shorter time to produce toxic components or to emit bad odor.

There is also known a process for having the oily substance included in cyclodextrin or cyclic glucan, as disclosed for example in Japanese Laid-open Patent Publications Nos.41395/1984, 34156/1985 or 33127/1986. This process again is disadvantageous since the oily substance is insufficient in stability although the emission of bad smell is inhibited by the effect of masking.

There is also known a lipid powder using a heat-coagulable protein as a coating film, as disclosed in Japanese Laid-open Patent Publication No.47643/1985. The powder has, however, a drawback that the oily substance is oxidized in the course of heat treatment.

A microcapsule produced by the coacervation process is disclosed in Japanese Laid-open Patent Publication No. 126016/1986. Although the oxygen barrier properties are improved by curing, the process disclosed therein does not lend itself to mass production because of the complicated operation and elevated costs.

SUMMARY OF THE INVENTION

It is therefore a principal object of the present invention to provide a lipid powder having a cross-linked coating thereon and the process for preparing the same, wherein the coating performance is significantly improved and the powder is easy to handle and high in oxidation stability.

It is another object of the present invention to provide a process for preparing lipid powders having cross-linked coatings thereon, which process allows a simplified operation and provides for mass production through reduction of manufacturing costs.

The above and other objects of the present invention will become more apparent as the present description proceeds.

In accordance with the present invention, there is provided a lipid powder having a cross-linked coating thereon comprising a core lipid powder and a water-soluble coating agent coating the core lipid powder, the water-soluble coating agent containing cross-linked protein.

In accordance with the present invention, there is also provided a process for preparing lipid powders each having a cross-linked coating thereon, comprising the steps of emulsifying lipid and a water-soluble coating agent containing protein to obtain an emulsion, adding a cross-linking agent for the protein to the emulsion to thereby cross-link the protein, atomizing and drying the emulsion containing the cross-linked protein to terminate the cross-linking reaction and to obtain lipid powders each coated with the water-soluble coating agent, and cooling the coated lipid powders.

DESCRIPTION OF THE PREFERRED EMBODIMENTS

The present invention will be explained in detail hereinbelow.

The lipid powder having a cross-linked coating thereon is comprised of a core lipid powder and a water-soluble coating agent coating the core lipid powder and containing cross-linked protein.

The lipid powder having thereon the cross-linked coating is constituted by a core lipid powder and a water-soluble coating agent containing cross-linked protein. Examples of the core lipids may include vegetable oils of natural origin, such as rape seed oil, soyabean oil, palm oil, rice bran oil, cotton seed oil, coconut oil, sunflower oil, peanut oil, olive oil, macademia nut oil or avocado oil, animal fats such as beef tallow, lard, horse tallow, mutton tallow, whale oil or fish oil, hydrogenated oil, fractionated oil or interesterification oil of the above mentioned vegitable oils and animal fats of natural origin, fatty acids obtained from oils and fats of natural origin, such as palmitic acid, stearic acid, palmitoleic acid, oleic acid, linolic acid, α-linoleic acid, γ-linoleic acid, arachidonic acid, eicosapentaenoic acid or docosahexaenoic acid, derivatives of the fatty acids, such as ethyl esters thereof, fat-soluble vitamins such as vitamin A, provitamin A, vitamin D, provitamin D, tocopherol or vitamin K, derivatives of the fat-soluble vitamins, fat-soluble flavor, seasoning oild, fat-soluble medicinal ingredients such as prostaglandin, surface active agents such as fatty acid monoglycerides, saccharose fatty acid esters, sorbitan fatty acid esters or propyleneglycol fatty acid esters and phospho- or glycolipids obtained naturally or by synthesis, either alone or in combination, as the occasion may demand.

It is essential that the cross-linked protein be contained in the water-soluble coating agent employed in the present invention. Examples of the protein may include milk protein such as casein, sodium caseinate or lactoalbumin, egg protein such as egg white albumin or ovomucoid, and animal protein such as collagen or gelatin. Any of the water-soluble protein hardeners may be employed as the cross-linking agent. Preferably, these cross-linking agents may be selected from the group consisting of aldehydes such as formalin or glutaraldehyde, tannic acid, alums and gluconic lactone. The water-soluble coating agent may include water-soluble substances in addition to protein. As the water-soluble substances, polysaccharides such as dextrin or cyclodextrin, gums such as gum arabic, xanthane gum or locust bean gum, celluloses such as microcrystalline cellulose or inorganic salts such as sodium hexametaphosphate, sodium secondary phosphate, sodium tertiary phosphate or table salt, may be used in suitable amounts, either alone or in combination.

The mixing ratio of the lipids, protein, cross-linking agent and the optional water-soluble substance in the lipid powder having thereon the cross-linked coating according to the present invention is desirably 10 to 400 parts by weight and preferably 20 to 200 parts by weight of protein, 0.05 to 10 parts by weight and preferably 0.1 to 3 parts by weight of the cross-linking agent and 0 to 400 parts by weight and preferably 20 to 100 parts by weight of the water-soluble substance to 100 parts by weight of the lipids.

With the amount of the protein less than 10 parts by weight, the coating performance is lowered. On the other hand, with the amount of the protein more than 400 parts by weight, workability is lowered due to increased viscosity. With the amount of the cross-linking agent less than 0.05 part by weight, sufficient cross-linking is not achieved. With the amount of the cross-linking agent more than 10 parts by weight, workability is lowered on account of gellation caused by excess cross-linking. With the amount of the water-soluble substance more than 400 parts by weight, the amount of the protein is correspondingly reduced and the coating performance is lowered.

In the preparation of the coated lipid powder according to the present invention, the lipids and the water-soluble coating agent containing protein are emulsified to obtain an emulsion. Preferably, an oil in water type emulsion is produced and homogenized by a homogenizer at a pressure of 80 to 250 kg/cm$^2$. It is noted that, in mixing and homogenizing the lipids and the water-soluble coating agent containing protein, preferably the water-soluble coating agent containing protein may previously be dissolved in a suitable solvent so that any insoluble substances are sufficiently dispersed in the resulting solution, after which the lipids are added to the solution and the whole mass is subsequently emulsified. The cross-linking agent for the protein is then added to the emulsion for cross-linking the protein. Preferably, a dilute solution of the cross-linking agent, for example, a solution containing 0.05 to 20 wt. % of the cross-linking agent, is added to the emulsion at the rate of 10 to 500 ml/min to carry out the reaction at 40° to 80° C. for 10 to 120 minutes for adjusting the viscosity of the emusion to 10 to 10,000 centipoise. The emulsion is then atomized and dried in situ to terminate the cross-linking reaction while producing lipid powders each coated with the water-soluble coating agent. Any suitable atomizing - drying device having a nozzle or rotary disk type atomizer, for example, may be used for the atomization and drying. Preferably, the drying is performed at an inlet temperature of 80° to 200° C. The concentration of the cross-linking agent is rapidly increased as a result of the atomization and drying so that the cross-linking reaction is terminated simultaneously with formation of the coated lipid powders.

According to the present invention, the coating performance of the lipid powder having the cross-linked coating thereon is significantly improved when compared with that of the conventional lipid powder, while the anti-oxidation properties of the powder is also improved since the contact of the powder contents with oxygen, ambient light, moisture and other ingredients may be prevented sufficiently from occurring, such that the usage and application of the lipid exhibiting physiological activities can be extended in the sectors of the foods and feedstuffs.

Also, when the core emits bad smell by nature, it becomes possible to suppress the smell. When the lipid powders are used as the feeds for pisciculture, water is not cotaminated because of the lower solubility of the powders in water. The useful lipids in the powder core is not dissolved in water until it is eaten by fish. The lipid powders of the present invention can be produced easily at lower costs and hence can be produced in larger quantities.

It will be appreciated from the foregoing that the present invention provides lipid powders having the cross-linked coating thereon, and the method for producing the same, according to which a number of technological merits not possible with the prior art practice can be realized.

EXAMPLES OF THE INVENTION

The present invention will be explained with reference to certain illustrative Examples.

EXAMPLE 1

An aqueous phase obtained by dissolving 1 kg of sodium caseinate in 10 kgs of water was mixed with an oil phase obtained by dissolving 0.1 kg of monoglycerine monostearate as an emulsifier in 4 kgs of rape seed oil. The resulting mixture was preliminarily emulsified at 70° C. and homogenized by a homogenizer at a pressure of 150 kg/cm$^2$. 1 kg of a 0.3% glutaraldehyde solution was slowly added dropwise to the emulsion under agitation and the resulting system was reacted for half an hour.

As the emulsion was atomized and dried in situ, the rape seed oil powders each having the cross-linked coating thereon were produced. These powders and the control powder samples each having no cross-linked coating thereon were separately stored in vessels each maintained at a constant temperature of 60° C. The oil contents were extracted periodically from the powders and the peroxide values thereof were measured. For extracting the oil contents, 10 g of the powders were admixed with 40 mls of chloroform and the resulting mass was subjected to ultrasonic wave processing for five minutes. The residual powders were filtered and the filtrate was concentrated and used as the measurement samples. The results are shown in Table 1.

TABLE 1

| Number of Days of Storage (in days) | Results of Oven Tests at 60° C. Peroxide Value | |
|---|---|---|
| | Cross-linked Coating | Non-cross-linked Coating |
| 10 | 5.6 | 7.1 |
| 20 | 9.8 | 17.1 |
| 30 | 20.3 | 29.7 |
| 40 | 32.8 | 83.1 |

It is seen from the above results that the rape seed oil in the lipid powders having the cross-linked coating thereon is improved in stability. An observation through a scanning type electron microscope (SEM) revealed that the lipid powder samples having the cross-linked coating had improved surface minuteness when compared with the control samples not having the cross-linked coating.

EXAMPLE 2

An aqueous phase obtained by dissolving 2 kgs of egg white albumin in 6 kgs of water was mixed with 2 kgs of EPA-concentrated fish oil containing 18% of eicosapentaenoic acid (EPA), produced by Nippon Oil & Fats Co. Ltd. under the trade name of "SUNOHEGA (Reg. TM) 18GA", as an oil phase. The resulting mixture was preliminarily emulsified at 40° C. and homogenized by a homogenizer at a pressure of 150 kg/cm$^2$. 1 kg of a 1% tannic acid solution was added slowly dropwise to the homogenized mass and the resulting system was reacted for 90 minutes.

The liquid emulsion was atomized and dried in situ to produce EPA lipid powders each having the cross-linked coating thereon. The produced powders and control sample powders each not having the cross-linked coating thereon were separately stored in vessels maintained at the constant temperature of 60° C., after which the oil contents were extracted from the powders in the same way as in Example 1, and the percentages of the residual eicosapentaenoic acid (EPA) in the oil contents were measured. The results are shown in Table 2.

TABLE 2

Results of Oven Tests at 60° C. (%)

| Number of Days of Storage (in days) | Percemtage of Residual EPA | |
|---|---|---|
| | Cross-linked Coating | Non-cross-linked Coating |
| 2 | 99.4 | 98.2 |
| 4 | 95.3 | 90.5 |
| 6 | 91.2 | 81.7 |
| 8 | 78.8 | 30.3 |

It is seen from the above results that EPA in the powder lipids having the cross-linked coating thereon has been improved in stability.

EXAMPLE 3

An aqueous phase obtained by dissolving 1 kg of egg white albumin in 4 kgs of water was mixed with 1 kg of 60% tocopherol oil produced by Nisshin-Seiyu KK under the trade name of Tocopherol 60 as an oil phase. The mixture was preliminarily emulsified at 40° C. and homogenized by a homogenizer at a pressure of 150 kg/cm$^2$. 1 kg of a 2% potash alum solution was added slowly to the homogenized mass under agitation and the resulting system was reacted for 90 minutes.

The liquid emulsion was atomized and dried in situ to produce the tocopherol lipid powders each having a cross-linked coating thereon. The produced powders and control sample powders each not having the cross-linked coating thereon were stored in vessels maintained at the constant temperature of 60° C. The oil contents were periodically extracted from the powders and the amounts of the tocopherol dimer produced upon oxidation was measured. In extracting tocopherol, the lipid powders were admixed with n-hexane, the resulting mass was processed with ultrasonic waves for five minutes, the residual lipid powder was filtered off and the filtrate was subjected to HPLC for measurement, using a column P-NH$_2$ manufactured by Shimazu Seisakusho, a moving bed of n-hexane -isopropyl ether 85-15 and a fluorescent light intensity sensor EM 328 nm, E$\times$300 nm. The results are shown in Table 3.

TABLE 3

Results of Oven Test Results at 60° C.

| Number of Days of Storage (in days) | Tocopherol Dimer Yield Rate (%) | |
|---|---|---|
| | Cross-linked Coating | Non-cross-linked Coating |
| 2 | 0.04 | 0.06 |
| 4 | 0.05 | 0.08 |
| 6 | 0.06 | 0.10 |
| 8 | 0.08 | 0.14 |

It is seen from the above results that tocopherol in the lipid powders having the cross-linked coating thereon has been improved in stability.

EXAMPLE 4

An aqueous phase obtained by dissolving 2kgs of sodium caseinate in 6 kgs of water was mixed with 2 kgs of ethyl linolate as an oil phase and the resulting mass was preliminarily emulsified at 60° C., which was then homogenized by a homogenizer at a pressure of 150 kg/cm$^2$. The resulting homogenized mass was slowly added to 1 kg of a 1% gluconic lactone solution and the resulting system was reacted for 90 minutes.

The liquid emulsion was atomized and dried in situ to produce ethyl linolate lipid powders each having a cross-linked coating thereon. The produced powders and control sample powders not having the cross-linked coating were placed in a YM type deterioration tester produced by Miyamoto Riken Kogyo KK and stored at 45° C. under the light of 15,000 luxes. The oil contents were extracted in the same way as in Example 1 and the peroxide values thereof were measured. The results are shown in Table 4.

TABLE 4

Results of YM Type Deterioration Tests

| Number of Days of Storage (in days) | Peroxide Values | |
|---|---|---|
| | Cross-linked Coating | Non-cross-linked Coating |
| 1 | 5.4 | 8.2 |
| 2 | 12.4 | 28.1 |
| 3 | 34.7 | 52.2 |
| 4 | 55.2 | 158.8 |

It is seen from the above results that ethyl linolate in the lipid powders having the cross-linked coating has been improved in stability.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. In a lipid powder having a cross-linked coating thereon comprising a core lipid powder and a water-soluble coating agent coating said core lipid powder, said water-soluble coating agent containing cross-linked protein, an wherein the improvement comprises said protein is crosslinked by tannic acid and is selected from the group consisting of milk protein, egg protein and mixtures thereof.

2. A lipid powder according to claim 1 wherein said lipid is selected from the group consisting of vegetable oils, animal fats, hydrogenated oils of said vegetable oil and the animal fats, fractionated oils of said vegetable oils and the animal fats, interesterification oils of said vegetable oils and the animal fats, fatty acids, derivatives of said fatty acids, fat-soluble vitamins, derivatives of said fat-soluble vitamins, phospholipids, glycolipids and mixtures thereof.

3. A lipid powder according to claim 2 wherein the lipid is selected from the group consisting of rape seed oil, soyabean oil, palm oil, rice bran oil, cotton seed oil, coconut oil, sunflower oil, peanut oil, olive oil, macademia nut oil, avocado oil, beef tallow, lard, horse tallow, mutton tallow, whale oil, fish oil, palmitic acid, stearic acid, palmitoleic acid, oleic acid, linolic acid, α-linoleic acid, γ-linoleic acid, arachidonic acid, eicosapentaenoic acid, docosahexaenoic acid, vitamin A, provitamin A, vitamin D, provitamin D, tocopherol, vitamin K and mixtures thereof.

4. A lipid powder according to claim 1 wherein said protein is selected from the group consisting of casein, sodium caseinate, lactoalbumin, egg white albumin, ovomucoid, and mixtures thereof.

5. A lipid powder according to claim 1 wherein said water-soluble coating agent further includes a water-soluble substance.

6. A lipid powder according to claim 5 wherein said water-soluble substance is selected from the group consisting of polysaccharides, gums, celluloses, inorganic salts and mixtures thereof.

7. A lipid powder according to claim 6 wherein said water-soluble substance is selected from the group consisting of dextrin, cyclodextrin, gum arabic, xanthane gum, locust bean gum, microcrystalline cellulose, sodium hexametaphosphate, sodium secondary phosphate, sodium tertiary phosphate, table salt and mixtures thereof.

8. A lipid powder according to claim 1 wherein 10 to 400 parts by weight of said protein are contained to 100 parts by weight of the lipid.

9. A lipid powder according to claim 5 wherein up to 400 parts by weight of said water-soluble substance are contained to 100 parts by weight of the lipid.

10. A lipid powder according to claim 1 wherein 0.05 to 10 parts by weight of said tannic acid is added to 100 parts by weight of the lipid 11. A lipid powder according to claim 1 wherein a 0.05 to 20 wt.% solution of the tannic acid is added at a rate of 10 to 500 ml/min for cross-linking the protein at 40° to 80° C. for 10 to 120 minutes.

* * * * *